(12) United States Patent
State

(10) Patent No.: US 9,216,101 B2
(45) Date of Patent: Dec. 22, 2015

(54) DUAL TAPER STENT PROTECTOR

(75) Inventor: Matt State, Rosemount, MN (US)

(73) Assignee: BOSTON SCIENTIFIC SCIME, INC., Maple Grove, MN (US)

(*) Notice: Subject to any disclaimer, the term of this patent is extended or adjusted under 35 U.S.C. 154(b) by 1603 days.

(21) Appl. No.: 11/775,332

(22) Filed: Jul. 10, 2007

(65) Prior Publication Data

US 2009/0018634 A1    Jan. 15, 2009

(51) Int. Cl.
| | |
|---|---|
| A61F 2/06 | (2013.01) |
| A61F 2/95 | (2013.01) |
| A61F 2/00 | (2006.01) |
| A61F 2/01 | (2006.01) |
| A61F 2/97 | (2013.01) |
| A61F 2/958 | (2013.01) |

(52) U.S. Cl.
CPC .............. A61F 2/95 (2013.01); A61F 2/0095 (2013.01); A61F 2/013 (2013.01); A61F 2/97 (2013.01); A61F 2002/9583 (2013.01); A61F 2250/0039 (2013.01); A61F 2250/0071 (2013.01)

(58) Field of Classification Search
CPC ......... A61F 2/95; A61F 2/0095; A61F 2/013; A61F 2/97; A61F 2250/0071; A61F 2250/0039; A61F 2002/9583
USPC ............ 623/1.11, 1.46, 1.12, 1.14, 1.16, 1.42
See application file for complete search history.

(56) References Cited

U.S. PATENT DOCUMENTS

| | | |
|---|---|---|
| 4,266,999 A | 5/1981 | Baier |
| 5,075,362 A | 12/1991 | Hofeldt et al. |
| 5,211,875 A | 5/1993 | Speer et al. |
| 5,342,307 A | 8/1994 | Euteneuer et al. |
| 5,556,383 A | 9/1996 | Wang et al. |
| 5,893,868 A | 4/1999 | Hanson et al. |
| 6,030,407 A | 2/2000 | Eidenschink |
| 6,110,146 A | 8/2000 | Berthiaume et al. |
| 6,132,450 A | 10/2000 | Hanson et al. |
| 6,152,944 A | 11/2000 | Holman et al. |
| 6,416,529 B1 | 7/2002 | Holman et al. |
| 6,545,097 B2 | 4/2003 | Pinchuk et al. |
| 6,764,504 B2 | 7/2004 | Wang et al. |
| 6,783,542 B2 | 8/2004 | Eidenschink |
| 6,827,731 B2 | 12/2004 | Armstrong et al. |

(Continued)

FOREIGN PATENT DOCUMENTS

| | | |
|---|---|---|
| WO | 9839056 | 9/1998 |
| WO | 0076425 | 12/2000 |
| WO | 0197715 | 12/2001 |

OTHER PUBLICATIONS

U.S. Appl. No. 11/775,340, filed Jul. 10, 2007 Holman et al.

(Continued)

Primary Examiner — Tuan V Nguyen
Assistant Examiner — Tin Nguyen
(74) Attorney, Agent, or Firm — Seager, Tufte & Wickhem, LLP

(57) ABSTRACT

A dual taper stent protector having a first stent covering region configured to cover a stent without substantially engaging the stent, a second covering region, and an engagement region for engaging a product mandrel removably disposed within a catheter shaft, and first and second tapered regions connecting the first stent covering region and the second stent covering region and the second covering region and the engagement region respectively, and to methods of making and using the same.

11 Claims, 4 Drawing Sheets

(56) References Cited

U.S. PATENT DOCUMENTS

| | | |
|---|---|---|
| 6,855,770 B2 | 2/2005 | Pinchuk et al. |
| 6,899,731 B2 | 5/2005 | Li et al. |
| 6,991,639 B2 | 1/2006 | Holman et al. |
| 7,000,770 B2 | 2/2006 | Clarke et al. |
| 7,014,654 B2 | 3/2006 | Welsh et al. |
| 7,096,554 B2 | 8/2006 | Austin et al. |
| 7,105,175 B2 | 9/2006 | Schwarz |
| 7,173,128 B2 | 2/2007 | Ravichandran et al. |
| 2001/0001128 A1 | 5/2001 | Holman et al. |
| 2002/0099431 A1* | 7/2002 | Armstrong et al. .......... 623/1.11 |
| 2003/0093086 A1 | 5/2003 | Briggs et al. |
| 2003/0125713 A1 | 7/2003 | McGlinch et al. |
| 2003/0149465 A1* | 8/2003 | Heidner et al. .............. 623/1.11 |
| 2003/0212410 A1 | 11/2003 | Stenzel et al. |
| 2004/0215169 A1 | 10/2004 | Li |
| 2005/0033404 A1 | 2/2005 | Eidenschink |
| 2005/0049671 A1 | 3/2005 | Wang et al. |
| 2005/0096724 A1* | 5/2005 | Stenzel et al. ............... 623/1.11 |
| 2005/0268573 A1 | 12/2005 | Yan |
| 2006/0015171 A1* | 1/2006 | Armstrong ................... 623/1.12 |
| 2006/0024426 A1 | 2/2006 | Akerman et al. |
| 2006/0260967 A1 | 11/2006 | Clarke et al. |
| 2006/0265044 A1* | 11/2006 | Gifford et al. ............... 623/1.11 |
| 2007/0250039 A1* | 10/2007 | Lobbins et al. ............... 604/523 |

OTHER PUBLICATIONS

U.S. Appl. No. 11/775,324, filed Jul. 10, 2007 Lindquist et al.
U.S. Appl. No. 11/545,253, filed Oct. 10, 2010 WasDyke et al.

* cited by examiner

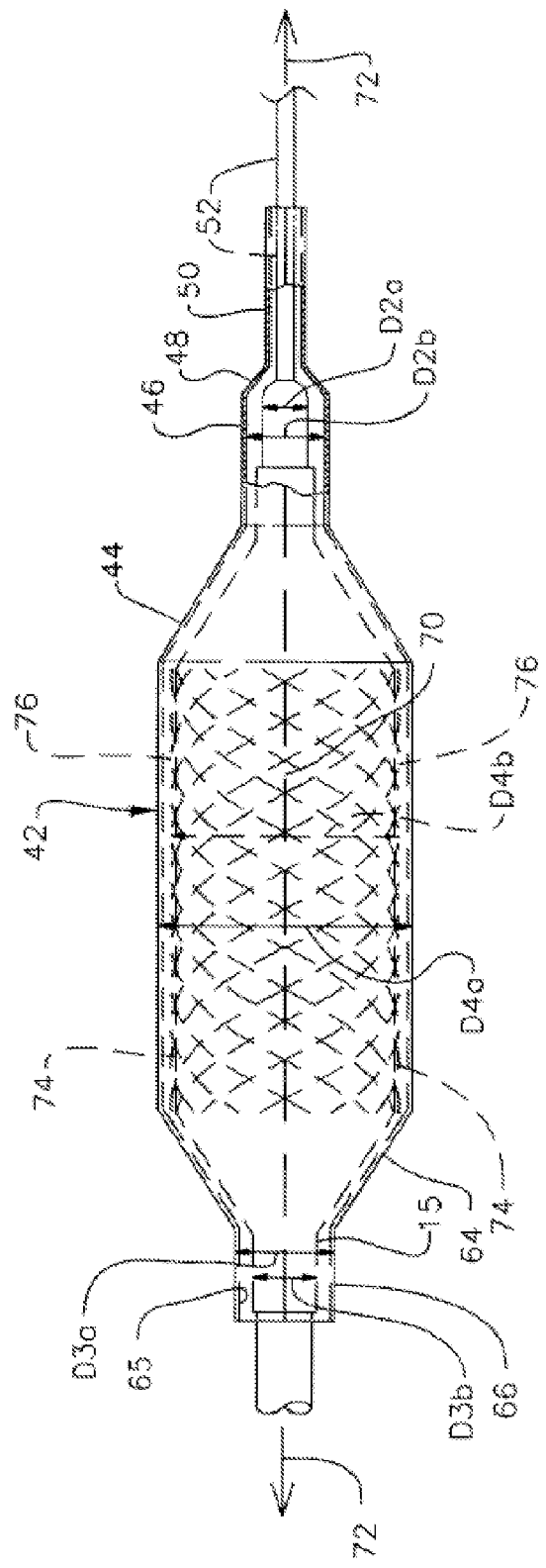

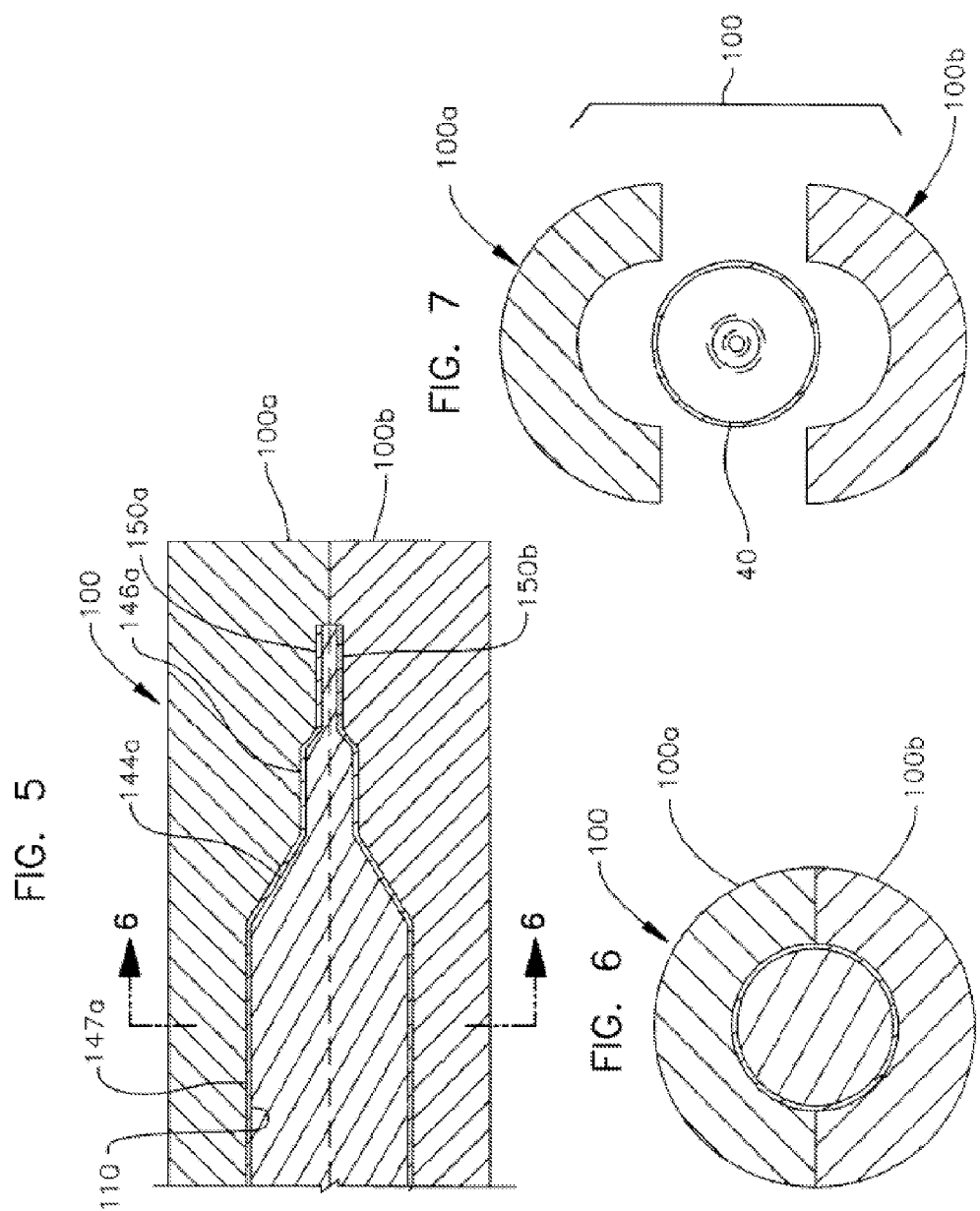

DUAL TAPER STENT PROTECTOR

FIELD OF THE INVENTION

The present invention relates to the field of catheter assemblies used for the delivery of medical devices, in particular stent delivery systems having stent protector means.

BACKGROUND OF THE INVENTION

A stent or similar device is an implantable medical device introduced into a body lumen and is well known in the art. Typically, a stent is implanted in a blood vessel at the site of a stenosis or aneurysm endoluminally, i.e. by so-called "minimally invasive techniques" in which the stent, in a radially reduced configuration, optionally restrained in a radially compressed configuration by a sheath and/or catheter, is delivered by a stent delivery system or "introducer" to the site where it is required. The introducer can enter the body from an access location outside the body, such as through the patient's skin, or by a "cut down" technique in which the entry vessel is exposed by minor surgical means. The device is enlarged radially at the treatment site.

Stents can be implanted in a variety of body lumens or vessels such as within the vascular system, urinary tracts, bile ducts, fallopian tubes, coronary vessels, secondary vessels, etc. Stents can be self-expanding, expanded by an internal radial force, such as when mounted on a balloon, or a combination of self-expanding and balloon expandable (hybrid expandable).

Stent protectors are used to protect the stent before the stent and catheter assembly are introduced and subsequently the stent deployed and implanted into a body lumen. The stent protector protects the stent from physical damage or contamination due to the transfer of unwanted material and is removed at the time of use to permit deployment of the stent. Examples of stent protectors are provided in commonly assigned U.S. Pat. Nos. 6,991,639, 6,783,542, 6,764,504, 6,416,529, 6,152,944, 5,893,868, and 5,342,307, each of which is incorporated by reference herein in its entirety.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

Without limiting the scope of the invention a brief summary of some of the claimed embodiments of the invention is set forth below. Additional details of the summarized embodiments of the invention and/or additional embodiments of the invention may be found in the Detailed Description of the Invention below.

SUMMARY OF THE INVENTION

The present invention relates to a stent protector having an improved design and to methods of making and using the same. The stent protectors according to the invention are designed to reduce or eliminate contact between the stent and the stent protector. The improved stent protector reduces the possibility of damaging either the stent protector material on the inner surface of the stent protector and/or any stent coatings on the outer surface of a stent by frictional resistance resulting during deposition of the stent protector over a stent delivery assembly.

In one aspect, the present invention relates to a catheter assembly including a catheter having a distal end and a proximal end, a stent disposed about the distal end. The catheter assembly further includes a stent protector having a first covering region disposed about the stent, a second covering region disposed about the catheter tip. For shipping and storage, the catheter assembly is further disposed about a product mandrel which is removed prior to use. The stent protector further includes an n engagement region which engages the product mandrel. The engagement region is remote from the first covering region so that the first covering region of the stent protector does not substantially engage the stent. When the stent protector is removed the product mandrel goes with it or visa versa.

In some embodiments, a first tapered region may connect the first stent covering region to the second catheter tip covering region and a second tapered region may connect the second catheter tip covering region to the engagement region. The second tapered region tapers down to the product mandrel so that upon crimping, an interference fit is created between the inner diameter of the engagement region of the stent protector and the product mandrel.

Likewise, the first tapered region of the stent protector tapers down to the second covering region so that, if desired, upon crimping an interference fit may likewise be created between the inner diameter of the second covering region and the catheter tip.

In the above embodiments, at the proximal end of the balloon, the stent protector need not be tapered, and can further include a flange at the proximal end.

At a minimum, the stent protector is engaged to the product mandrel.

Alternative designs may include engagement at a catheter distal tip, and engagement at a catheter outer shaft at the proximal end of the protector.

The improved stent protectors according to the invention are particularly suitable for stents having coatings, such as drug eluting coatings, disposed thereon.

These and other aspects, embodiments and advantages of the present invention will become immediately apparent to those of ordinary skill in the art upon review of the Detailed Description and Claims to follow.

BRIEF DESCRIPTION OF THE DRAWINGS

FIG. 4 is a partial side view of the distal end of a catheter assembly with parts shown in hidden line illustrating another embodiment of the stent protector of the invention.

FIG. 5 is a portion of an injection mold for forming a stent protector according to the invention.

FIG. 6 is a radial cross-section taken at section 6-6 in FIG. 5.

FIG. 7 is a radial cross-section taken at section 6-6 illustrating the mold in an open configuration, showing both mold halves and the stent protector released therefrom.

DETAILED DESCRIPTION OF THE INVENTION

Figure 1:
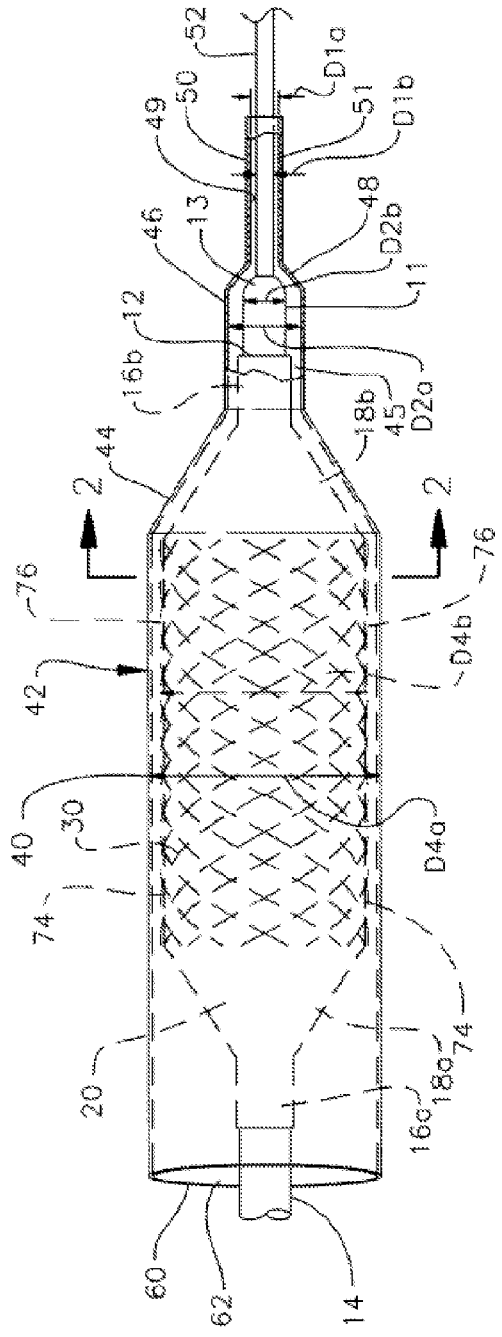
FIG. 1 is a partial side view showing the distal end of a catheter assembly with parts shown in hidden line illustrating one embodiment of a stent protector of the invention.

While this invention may be embodied in many different forms, there are described in detail herein specific preferred embodiments of the invention. This description is an exemplification of the principles of the invention and is not intended to limit the invention to the particular embodiments illustrated.

All US patents and applications and all other published documents mentioned anywhere in this application are incorporated herein by reference in their entirety. Any copending patent applications, mentioned anywhere in this application are also hereby expressly incorporated herein by reference in their entirety.

For the purposes of this disclosure, like reference numerals in the figures shall refer to like features unless otherwise indicated.

Turning now to the figures, FIG. 1 is a partial side view of the distal end of a catheter assembly 10 with parts shown in hidden line illustrating one embodiment of a stent protector 40 according to the invention. Catheter assembly 10 has an inner shaft 12 and an outer shaft 14. Distal tip 13 is shown at the end of the inner shaft 12. The distal end of each shaft is shown in FIG. 1. Balloon 20 is disposed about the distal end of the outer shaft 14 at the balloon proximal end 32 and is disposed about the distal end of the inner shaft 12 at the balloon distal end 34. Balloon 20 may be secured to the inner shaft 12 and the outer shaft 14 at its waist portions 16a, 16b using any suitable method known in the art such as welding, adhesively, etc.

Figure 2:
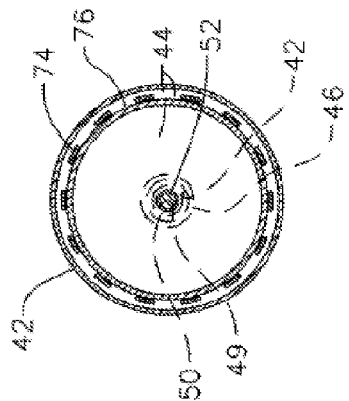
FIG. 2 is a radial cross-section taken at section 2-2 in FIG. 1.

Stent 30 is disposed about balloon 20 in the body region 22 of balloon 20. FIG. 2 is a radial cross-section taken at section 2-2 in FIG. 1.

Stent protector 40 is disposed about balloon 20 and stent 30. Stent protector 40 is designed so as to engage the product mandrel 52. The outer surface (outer diameter) of the product mandrel 52 is engaged by the inner surface (inner diameter) of the stent protector 40. When stent protector 40 is removed, the product mandrel 52 is removed as well. In this embodiment, stent protector 40 has a first stent covering region 42, a first tapered region 44, a second covering region 46 which covers catheter distal tip 13, a second tapered region 48 and at least one engagement region 50. Engagement region 50 engages the product mandrel 52 which is removed prior to use, typically by the practitioner performing the procedure. Stent protector 40, being engaged to product mandrel 52, is likewise removed simultaneously. The second tapered region 48 tapers down to the engagement region 50 which is crimped about the product mandrel 52 to create an interference fit between the outer surface (outer diameter) of the product mandrel 52 inner surface 49 (inner diameter) of the engagement region 50 of the stent protector 40 and the product mandrel 52.

In another embodiment, the second covering region 46 may optionally engage the catheter tip 13. In this embodiment, the first tapered region 44 tapers down to the second covering region 46 which is crimped so as to create an interference fit between the inner diameter 54 of the second covering region 46 and the catheter tip 13 (outer diameter). Likewise, in embodiments wherein a coating, such as a lubricious coating is disposed on the catheter tip 13, it may be desirable for engagement of the stent protector 40 to engage the catheter assembly only at the engagement 50 region which engages the product mandrel 52.

FIG. 2 is a radial cross-section taken at section 2-2 in FIG. 1.

Figure 3:
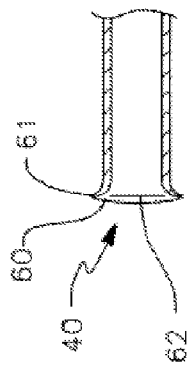
FIG. 3 is a partial side view of the proximal end of a stent protector similar to that shown in FIG. 1.

In the above embodiments, the proximal end 32 of the stent protector 40 is shown having a non-tapered configuration. In this embodiment, the wall 60 of said stent protector defines the lumen 62 of the stent protector 40 at the proximal end 32 may be flared out slightly away from the catheter assembly 10 about which it is disposed. This feature is shown in FIG. 3. Hereinafter, said feature is referred to as a flange 61. Thus, in this embodiment, the stent protector 40 has an open proximal end 32. This flared rim 60 can facilitate placement of the stent protector 40 over the catheter assembly 10 and/or can facilitate removal of the stent protector at the time of use.

In another embodiment shown in FIG. 4, stent protector 40 may have a third tapered region 64 at the proximal end 32 which tapers to the balloon waist 16a wherein a third covering region 66 of stent protector 40 covers balloon waist 16a. Upon crimping, an interference fit may be created between the inner diameter 68 of the third covering region 66 of the stent protector 40 and the balloon waist 441 disposed about the outer catheter shaft 14. In this embodiment, the stent protector 40 is further designed with a removal means such as perforations 70, in this embodiment shown parallel with the longitudinal axis 72 of the catheter assembly 10, so that the stent protector 40 may be peeled away from the catheter assembly 10 at the time of use.

Thus, in this embodiment, the stent protector 40 has a proximal end 32 which is substantially closed around the balloon proximal waist 44a and the outer catheter shaft 14, further restricting movement of the stent protector 40.

Any suitable method of forming perforations 70 in the stent protector 40 may be employed. For example, a laser may be employed for formation of the perforations 70 including, for example, UV Excimer lasers and Nd:Yag lasers. Other cutting methods include, but are not limited to, the use of razor blades, stamping dies, etc.

In any of the above embodiments, the first stent covering region 42 has an inner diameter $D_{4a}$ which is greater than the outer diameter $D_{4b}$ of the stent so that no friction is created between the inner surface 74 of the stent protector 40 and the outer surface 76 of the stent 30. The enlarged diameter $D_{4a}$ of the first stent covering region 42 of the stent protector 40 covers the stent 20 and maintains a space (i.e. the region between the widened wall portion and the stent) between the inner surface 74 of the first stent covering region 42 and the stent 30 such that the inner surface 74 of the first stent covering region 42 does not engage the stent 30 during normal storage or removal.

The stent protectors as disclosed herein can be formed of any of a wide variety of suitable stent protector materials, for example, polymer materials including both thermoplastic elastomers and non-elastomers, and thermosetting materials. Examples of suitable polymer materials include, but are not limited to fluropolymers such as polytetrafluoroethylene (PTFE) and FEP, polyamides, i.e. nylons, silicones, and so forth.

Heat shrinkable materials may also be employed wherein the material is heat shrunk only in the desirable regions of the stent protector such as the engagement region 50, the second covering region 46, the third covering region 66, or some combination thereof.

Heat shrinkable materials are typically thermoplastic, although in some instances thermoset materials may be employed, and include both elastomeric and non-elastomeric polymer materials. Suitable examples include, but are not limited to, polyolefins including, for example, homopolymers, copolymers and terpolymers of ethylene and propylene, fluoropolymers such as fluorinated ethylene-propylene (FEP), polytetrafluoroethylene (PTFE), polyvinylidene fluorides (PVFD) such as Kynar® PVFD's including Kynar® 500 available from Arkema Inc. in Philadelphia, Pa., copolymers of hexafluoropropylene (HFP), terpolymers of tetrafluoroethylene (TFE), ethylene-chlorotrifluoroethylene (ECTFE), VDF and HFP as well as perfluoromethylvinylether (PMVE), Viton® fluoropolymer elastomers available from Du Pont Performance Elastomers in Wilmington, Del., polyvinyl chloride (PVC), neoprene, silicon elastomers, polyamides including the nylons, polyether-block-amides, etc.

The stent protector may be formed using any suitable method known in the art. In one embodiment, a tubular member having a diameter substantially equal to the resultant diameter of the first stent covering region may be disposed about the catheter assembly where desired. In one embodiment, the engagement region may be formed by heat shrinking the material. In other embodiments, the tapered regions, the second covering region, the third covering region, and any combination thereof may also be created by heating shrinking the stent protector around the assembly in those regions only.

In one specific embodiment, the stent protector is formed using an injection molding process. For illustration only, a longitudinal cross-section of a portion of one embodiment of an injection mold 100 is shown in FIG. 5. In this embodiment, cavity 110 of mold 100 has a first half 100a and a second half 100b, each having first covering regions 142a, 142b, first tapered regions 144a, 144b, second covering regions 146a, 146b and engagement regions 150a, 150b for formation of the stent protector.

FIG. 6 is a radial cross-section taken at section 6-6 in FIG. 5. FIG. 7 is a radial cross-section showing the mold 100 in an open configuration with the stent protector 40 being released.

Figure 8:
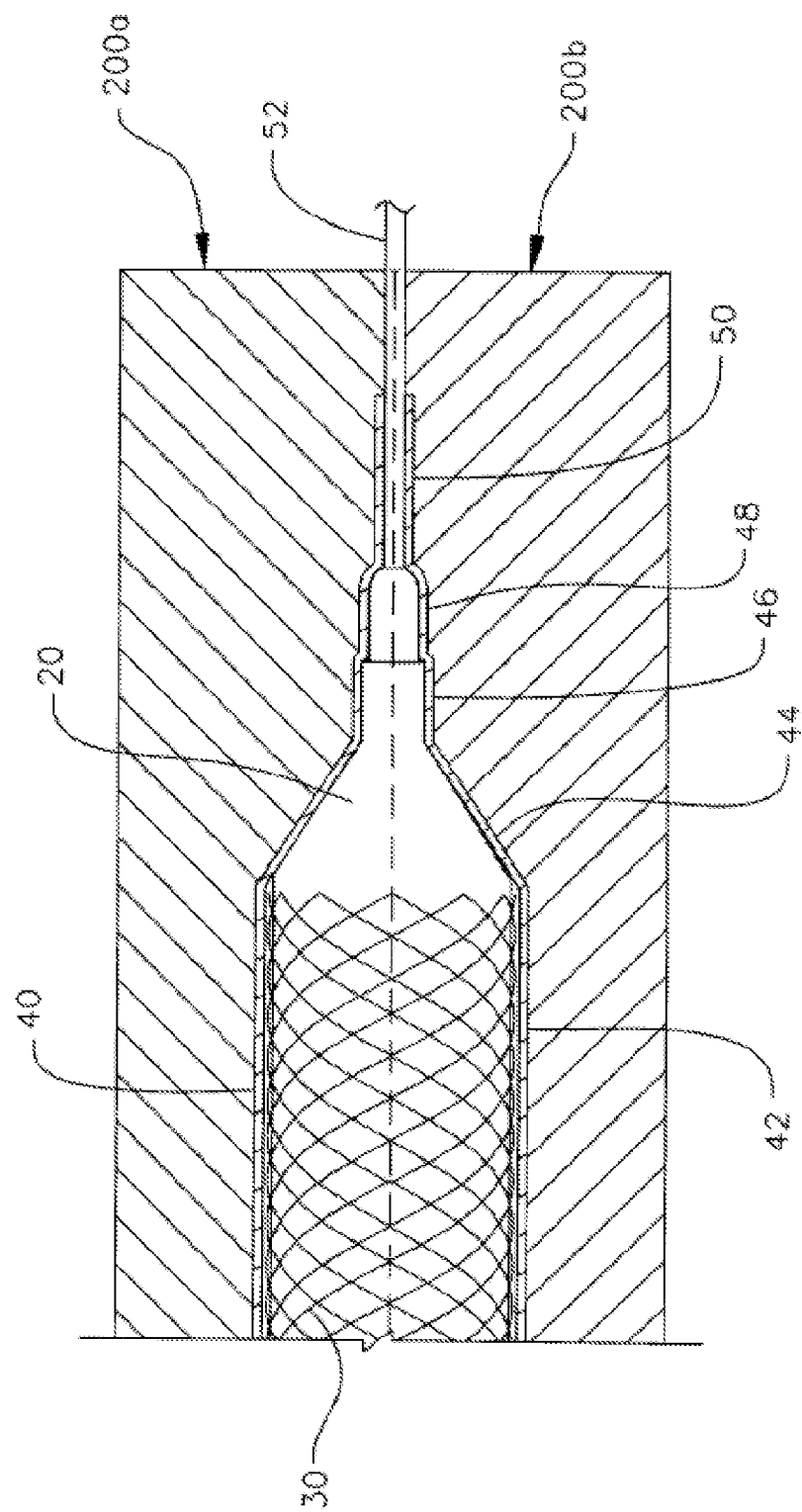
FIG. 8 is a portion of a crimper for forming a stent protector about a catheter assembly.

The stent protector 40 may also be crimped about the catheter assembly. FIG. 8 is a longitudinal cross-section wherein heated crimpers 200a and 200b are applied externally to the catheter assembly and pressure and heat are used to conform the stent protector 40 about the catheter assembly.

These are only examples of methods of making the stent protector disclosed herein. The invention is not limited by the method employed and other methods may be used as well.

The present invention finds particular utility wherein stent coatings are employed. Stent coatings may incorporate a polymer material. There are any suitable polymer materials which are employed in stent coatings are such polymer materials are well known in the art.

In some embodiments, the stent coating may include bioresorbable polymers. Examples of bioresorbable polymers include, but are not limited to, polyhydroxyalkanoates such as polyhydroxyvalerate (PHV), polyhydroxybutyrate (PHB), poly(hydroxybutyrate-co-valerate) (PHBV) and polycaprolactone (PCL), poly(L-lactic acid) (PLA), poly(lactide-co-glycolide) (PLGA), polydioxanone, polyorthoesters, polyanhydrides, poly(glycolic acid), poly(D,L-lactic acid), poly(glycolic acid-co-trimethylene carbonate), polyphosphoesters, polyphosphoester urethanes, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen, hyaluronic acid, etc., and mixtures thereof.

Some of these polymers may be susceptible to hydrolysis in the presence of moisture.

Lubricious coatings are also commonly employed on various components of a catheter assembly and are also well known in the art. Lubricious coatings include both hydrophilic and non-hydrophilic polymer materials. Commonly employed hydrophilic polymer materials include those referred to in the art as hydrogels.

Lubricious coatings may be employed on any component of the catheter assembly and are commonly employed on the balloon body, waist and cones, or any combination thereof, as well as on the outer catheter shaft and the catheter distal tip 13. Where a lubricious coating is employed on the distal tip 13, it may be desirable for the stent protector 40 to engage only the product mandrel 52. Suitably, in such an embodiment the inner diameter $D_{2a}$ of the second covering region 46 of the stent protector may suitably be greater than the outer diameter $D_{2b}$ of the catheter distal tip 13 so as to minimize damage to the lubricious coating.

In other embodiments, the second covering region 46 may be crimped onto the catheter distal tip 13 as discussed previously.

Any of the coatings may incorporate a therapeutic agent therein. The terms, "therapeutic agent", "drug", "pharmaceutically active agent", "pharmaceutically active material", "beneficial agent", "bioactive agent", and other related terms may be used interchangeably herein and include genetic therapeutic agents, non-genetic therapeutic agents and cells. A drug may be used singly or in combination with other drugs. Drugs include genetic materials, non-genetic materials, and cells.

Examples of drugs can be found in commonly assigned U.S. Pat. Nos. 7,105,175, 7,014,654, 6,899,731, 6,855,770 and 6,545,097, each of which is incorporated by reference herein in its entirety, and in commonly assigned U.S. Patent Application Publication No. 2004/0215169, the entire content of which is incorporated by reference herein.

The above disclosure is intended to be illustrative and not exhaustive. This description will suggest many variations and alternatives to one of ordinary skill in this art. Those familiar with the art may recognize other equivalents to the specific embodiments described herein which equivalents are also intended to be encompassed by the claims.

The invention claimed is:

1. A catheter assembly comprising:
   at least one catheter shaft having a distal end and a proximal end, a distal tip disposed at the distal end and a longitudinal axis;
   a stent disposed about the distal end of the catheter shaft;
   a product mandrel, the product mandrel removably disposed within the catheter shaft, and exposed at the distal end of the catheter shaft and distal of the distal tip;
   a stent protector having an inner surface and an outer surface and having a proximal end and a distal end, the stent protector having a first stent covering region having a first inner diameter defined by the inner surface and disposed about the stent without substantially engaging the stent, a second stent covering region having a second inner diameter defined by the inner surface which is less than the first inner diameter located distal of the first stent covering region disposed about the catheter shaft distal tip, a first connecting region connecting the first stent covering region and the second stent covering region, an engagement region having a third inner diameter defined by the inner surface which is less than the second inner diameter, the engagement region engaging the product mandrel, and a second connecting region connecting the second stent covering region and the engagement region and wherein the product mandrel and the stent protector are removed from the catheter assembly prior to use.

2. The catheter assembly of claim 1 wherein the first connecting region has an inner diameter that tapers between the first stent covering region and the second stent covering region and the second connecting region has an inner diameter that tapers between the second stent covering region and the engagement region.

3. The catheter assembly of claim 2, the first connecting region having an outer diameter defined by an outer surface wherein the outer diameter of the first connecting region tapers between the first stent covering region and the second stent covering region and the second connecting region having an outer diameter defined by an outer surface wherein, the outer diameter of the second connecting region tapers between the second stent covering region and the engagement region.

4. The catheter assembly of claim 1 wherein said second stent covering region of said stent protector engages said catheter distal tip.

5. The catheter assembly of claim 1 further comprising a first tapered region and a second tapered region, the second stent covering region, the first tapered region, the engagement region and the second tapered region are located distally of said first stent covering region the first tapered region is adjacent to and distal of the first stent covering region, the second stent covering region is adjacent to and distal of the first tapered region, the second tapered region is adjacent to and distal of the second stent covering region, the engagement region is adjacent to and distal of the second tapered region, and the proximal end of the stent protector is non-tapered.

6. The catheter assembly of claim 5 wherein said stent protector comprises a flange at said proximal end of said stent protector.

7. The catheter assembly of claim 1 wherein the proximal end of the stent protector comprises at least one tapered region.

8. The catheter assembly of claim 1 further comprising an expandable balloon member having a body region, a distal waist region, a distal cone region, a proximal waist region, a proximal cone region, and a longitudinal axis, and wherein said proximal end of said stent protector has a third tapered region and a third covering region, the third covering region engages said proximal waist region of said balloon.

9. The catheter assembly of claim 8 wherein said stent protector further comprises perforations from said proximal end to said distal end of said stent protector for facilitating removal of said stent protector from said catheter assembly.

10. The catheter assembly of claim 1 wherein said stent comprises a drug eluting coating.

11. The catheter assembly of claim 1 wherein said catheter distal tip comprises a lubricious coating.

* * * * *